May 24, 1960 F. W. ANDERSON Plant Pat. 1,947

NECTARINE TREE

Filed Aug. 17, 1959

WITNESS

Addison E. Avery

INVENTOR

Frederic W. Anderson

Webster & Webster

ATTYS.

United States Patent Office

Plant Pat. 1,947
Patented May 24, 1960

1,947

NECTARINE TREE

Frederic W. Anderson, Merced, Calif., assignor to Stark Bro's Nurseries and Orchards Co., Louisiana, Mo., a corporation of Missouri Filed Aug. 17, 1959, Ser. No. 834,364

1 Claim. (Cl. 47—62)

This invention relates to a new and distinct variety of nectarine tree which bears yellow-fleshed freestone fruit having yellow skin overspread and mottled to a substantial extent with red. The variety is of the type embraced by group 112 of the classification by Caillavet and Souty, Monographie des Principales Variétés de Pêchers, 1950 edition, page 46.

The instant variety of nectarine tree is quite similar to the Sun Grand (United States Plant Patent No. 974) in size, color, and eating and shipping qualities of the fruit, but—in comparison—has reniform instead of globose glands on the leaves, and the fruit ripens approximately ten days later. Such later ripening period is of substantial commercial advantage, as it will extend the marketing season of the type of nectarine represented by the Sun Grand, and which—at present—is the most extensively grown freestone nectarine in California.

The herein claimed variety of nectarine tree was originated by me in my experimental orchard located near Merced, California, as an open-pollinated seedling of an unnamed seedling of the Sun Grand nectarine. The parent tree was maintained by me under careful and continuing observation and when it reached maturity I recognized its distinct and desirable characteristics and selected it for reproduction.

Asexual reproduction of the variety was accomplished by me, in my experimental orchard located as aforesaid, by topworking on mature orchard trees; such reproductions having run true in all respects.

Figures 1, 2:
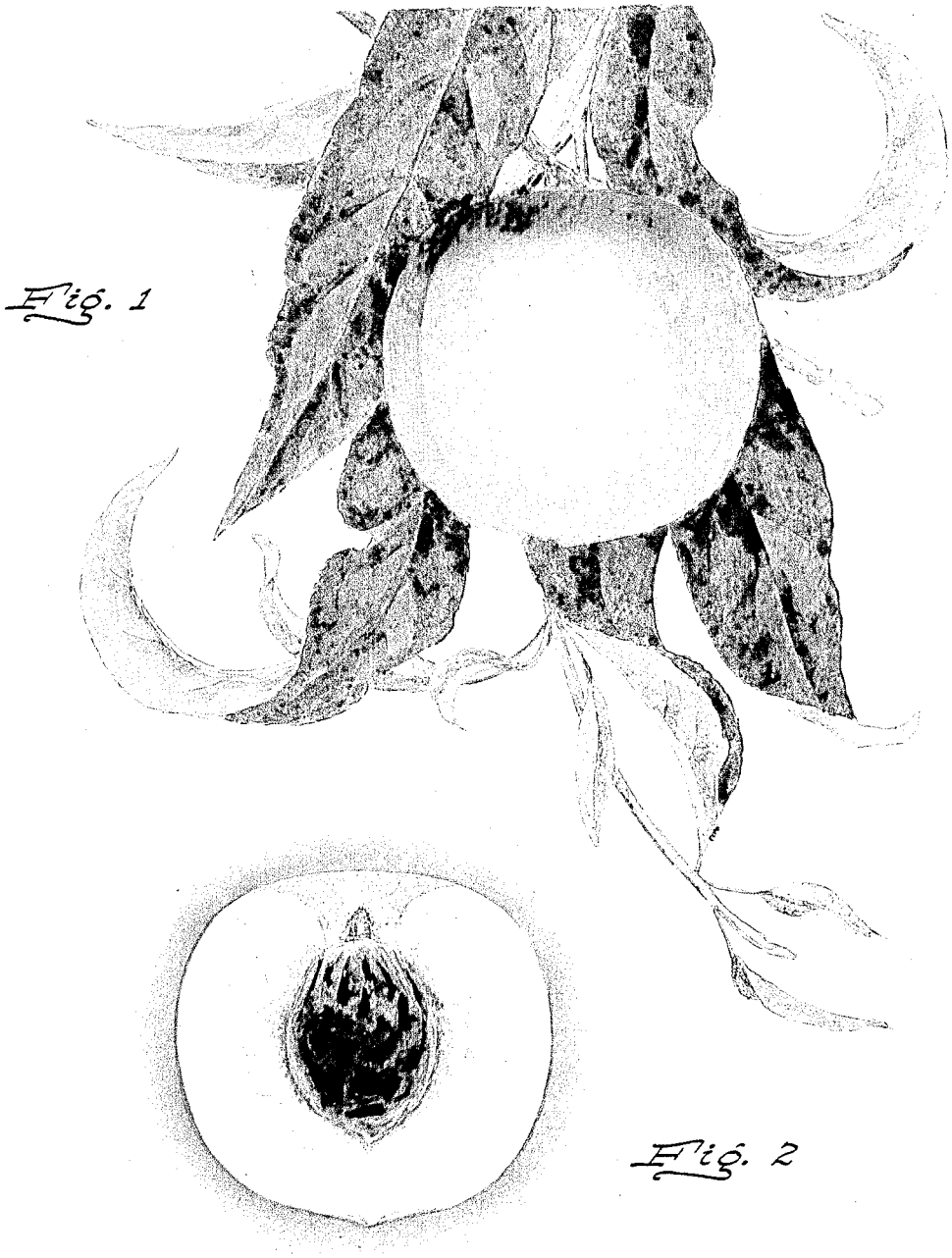
Fig. 1 is an elevation showing one of the nectarines, together with a twig and leaves.
Fig. 2 is a sectional elevation of one of the nectarines with the stone remaining in place.

Referring to pomological details of this new and distinct variety of nectarine tree and its fruit, the following is an outline description thereof; all major color plate identifications being by reference to Maerz and Paul Dictionary of Color.

Tree:
- *Size.*—Large to medium.
- *Vigor.*—Vigorous.
- *Form.*—Upright to spreading.
- *Production.*—Productive.
- *Bearing.*—Regular bearer.

Trunk:
- *Size.*—Medium.
- *Texture.*—Medium.

Branches: Size—medium.

Leaves:
- *Size.*—Large to medium.
- *Margin.*—Crenate.
- *Glands.*—Average number—usually two on petiole and two or more on blade. Reniform.
- *Color.*—Top side—medium green (23–L–6. Under side—lighter green (21–K–6).

Flower buds: Size—large.

Flowers:
- *Blooming period.*—Medium compared with other varieties.
- *Size.*—Large.

Fruit:
- *Maturity when described.*—Eating ripe—July 22, 1958.
- *Date of first picking.*—July 15, 1958.
- *Date of last picking.*—July 28, 1958.
- *Size.*—Uniform; large to medium. Average diameter axially—2⅝". Average transversely in suture plane—2 11/16".
- *Form.*—Symmetrical; globose.
- *Suture.*—Distinct; shollow.
- *Cavity.*—Rounded.
- *Base.*—Rounded.
- *Apex.*—Short; depressed.

Skin:
- *Thickness.*—Thick to medium.
- *Texture.*—Medium.
- *Tendency to crack.*—None.
- *Color.*—Yellow (9–L–5), overspread and mottled to a substantial extent with red (1–A–12 to 1–L–10), shading therefrom to darker red (7–L–6).

Flesh:
- *Texture.*—Firm; meaty.
- *Ripens.*—Even.
- *Flavor.*—Subacid.
- *Eating quality.*—Good to best.
- *Color.*—Yellow (9–L–2 to 9–L–5), streaked with red (1–L–3) adjacent the stone.

Stone:
- *Type.*—Free.
- *Size.*—Medium.
- *Form.*—Oval.
- *Sides.*—Equal.
- *Tendency to split.*—Slight.
- *Color.*—Predominately brown (7–L–12).

Use: Market; long distance shipping.

Shipping quality: Good.

The tree and its fruit here described may vary in slight detail due to climatic and soil conditions under which this variety may be grown; the present description being of the variety as grown in the Central Valley of California.

The following is claimed:

A new and distinct variety of nectarine tree, as illustrated and described, which bears freestone fruit having yellow flesh streaked with red adjacent the stone, the skin being yellow, overspread and mottled to a substantial extent with red; the variety being similar to the Sun Grand in size, color, and eating and shipping qualities of the fruit, but—in comparison—has reniform instead of globose glands on the leaves, and the fruit ripens ten days later.

No references cited.